(12) United States Patent
Kobayashi et al.

(10) Patent No.: US 9,645,065 B2
(45) Date of Patent: May 9, 2017

(54) FLOW ANALYZER AND FLOW ANALYSIS METHOD

(71) Applicants: The University of Tokyo, Tokyo (JP); JEOL Ltd., Tokyo (JP)

(72) Inventors: Shu Kobayashi, Tokyo (JP); Kenji Takasugi, Tokyo (JP)

(73) Assignees: The University of Tokyo, Tokyo (JP); JEOL Ltd., Tokyo (JP)

( * ) Notice: Subject to any disclaimer, the term of this patent is extended or adjusted under 35 U.S.C. 154(b) by 84 days.

(21) Appl. No.: 14/721,254

(22) Filed: May 26, 2015

(65) Prior Publication Data
US 2015/0346070 A1 Dec. 3, 2015

(30) Foreign Application Priority Data

May 27, 2014 (JP) ................................. 2014-108869

(51) Int. Cl.
*G01N 11/06* (2006.01)
*G01N 11/02* (2006.01)
*G01N 24/08* (2006.01)
*G01N 11/00* (2006.01)

(52) U.S. Cl.
CPC ............ *G01N 11/02* (2013.01); *G01N 24/08* (2013.01); *G01N 24/085* (2013.01); *G01N 24/088* (2013.01); *G01N 2011/0086* (2013.01); *Y10T 436/117497* (2015.01)

(58) Field of Classification Search
CPC .......... B01J 13/02; G01N 11/02; G01N 11/06
See application file for complete search history.

(56) References Cited

U.S. PATENT DOCUMENTS 5,458,808 A * 10/1995 Suggitt ..................... C01B 3/36
252/373

FOREIGN PATENT DOCUMENTS

JP          2001272390 A    10/2001

* cited by examiner

*Primary Examiner* — Paul Hyun
(74) *Attorney, Agent, or Firm* — The Webb Law Firm

(57) ABSTRACT

A flow analyzer includes a flow container, a fluid-introducing section that introduces an introduction target fluid into the flow container, a fluid control section that performs a control process that cyclically changes the flow rate or the fluid pressure of the introduction target fluid that is introduced into the flow container from the fluid-introducing section, a discharged fluid analysis section that performs a component analysis process on a discharged fluid that has been discharged from the flow container, and a frequency analysis section that performs a frequency analysis process on a discharge profile, the discharge profile being obtained from control information about the introduction target fluid and analysis results for the discharged fluid, and representing the relationship between the component ratio in the discharged fluid and time.

12 Claims, 10 Drawing Sheets

FLOW ANALYZER AND FLOW ANALYSIS METHOD

Japanese Patent Application No. 2014-108869, filed on May 27, 2014, is hereby incorporated by reference in its entirety.

BACKGROUND OF THE INVENTION

The present invention relates to a flow analyzer and a flow analysis method.

A flow reactor is a device that includes a channel reactor that utilizes a column or the like as a flow channel, and causes a reactant introduced into the flow channel to undergo a chemical reaction to obtain the desired product.

A normal-pressure flow system having a structure similar to that of the flow reactor may utilize a method that switches the introduction target fluid after the flow system has reached an equilibrium state, and measures the adsorption curve and the desorption curve of the fluid with respect to a polymer or the like provided inside the flow system to analyze the coefficient of diffusion that is attributed to adsorption-desorption equilibrium.

For example, JP-A-2001-272390 discloses a method that introduces helium gas or the like into a flow system that shows adsorption-desorption equilibrium to mainly measure a diffusion phenomenon due to desorption.

The method disclosed in JP-A-2001-272390 can measure the absorption amount and the coefficient of diffusion of gas with respect to a polymer material. However, the functional form of the response function obtained by the measurement is an exponential decay function (when desorption is predominant) or a complementary error function (when an adsorption-desorption equilibrium state is reached). Therefore, it is necessary to use an unstable irreversible analysis method such as an inverse Laplace transform in order to calculate the absorption amount and the coefficient of diffusion of gas from the measurement results.

Specifically, the method disclosed in JP-A-2001-272390 has a problem in that analysis that utilizes an irreversible analysis routine based on an exponential response is required to analyze the state inside the flow reactor in detail, and time-consuming calculations are necessary.

SUMMARY

Several aspects of the invention may provide a flow analyzer and a flow analysis method that make it possible to easily evaluate the state inside a flow container.

According to a first aspect of the invention, there is provided a flow analyzer including:
a flow container;
a fluid-introducing section that introduces an introduction target fluid into the flow container;
a fluid control section that performs a control process that cyclically changes a flow rate or a fluid pressure of the introduction target fluid that is introduced into the flow container from the fluid-introducing section;
a discharged fluid analysis section that performs a component analysis process on a discharged fluid that has been discharged from the flow container; and
a frequency analysis section that performs a frequency analysis process on a discharge profile, the discharge profile being obtained from control information about the introduction target fluid and analysis results for the discharged fluid, and representing a relationship between a component ratio in the discharged fluid and time.

According to a second aspect of the invention, there is provided a flow analysis method including:
a fluid control step that performs a control process that cyclically changes a flow rate or a fluid pressure of an introduction target fluid that is introduced into a flow container;
a discharged fluid analysis step that performs a component analysis process on a discharged fluid that has been discharged from the flow container; and
a frequency analysis step that performs a frequency analysis process on a discharge profile, the discharge profile being obtained from control information about the introduction target fluid and analysis results for the discharged fluid, and representing a relationship between a component ratio in the discharged fluid and time.

Figure 1:
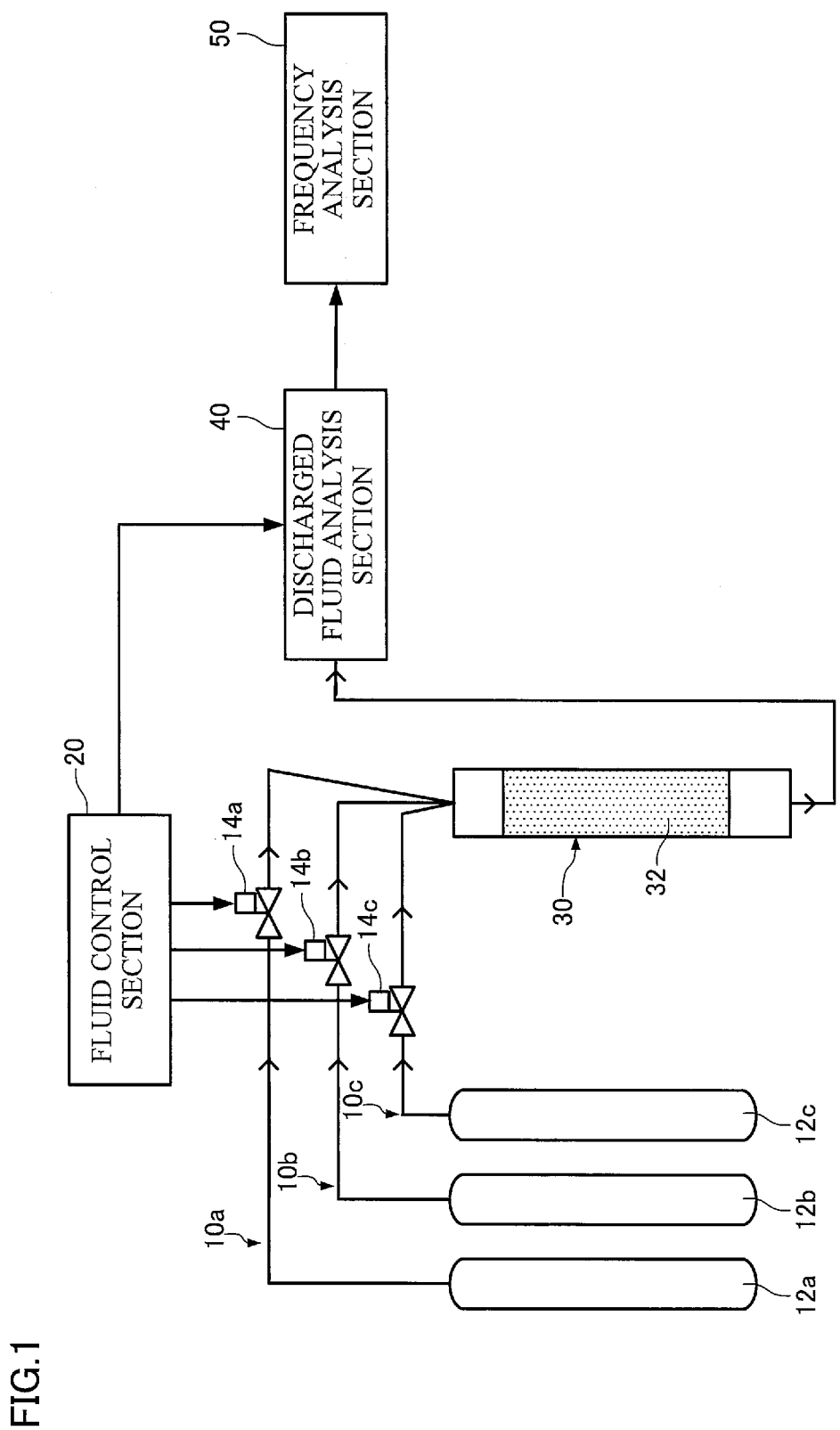
FIG. 1 schematically illustrates the configuration of a flow analyzer according to the first embodiment.

DETAILED DESCRIPTION OF THE EMBODIMENT (1) According to one embodiment of the invention, there is provided a flow analyzer including:
a flow container;
a fluid-introducing section that introduces an introduction target fluid into the flow container;
a fluid control section that performs a control process that cyclically changes a flow rate or a fluid pressure of the introduction target fluid that is introduced into the flow container from the fluid-introducing section;
a discharged fluid analysis section that performs a component analysis process on a discharged fluid that has been discharged from the flow container; and
a frequency analysis section that performs a frequency analysis process on a discharge profile, the discharge profile being obtained from control information about the introduction target fluid and analysis results for the discharged fluid, and representing a relationship between a component ratio in the discharged fluid and time.

Since the flow analyzer can evaluate the state inside the flow container by performing the frequency analysis process on the discharge profile, it is possible to easily evaluate the state inside the flow container as compared with the case of evaluating the state inside the flow container using an irreversible analysis process such as an inverse Laplace transform.

(2) In the above flow analyzer, the fluid control section may perform a square-wave control process on the flow rate or the fluid pressure of the introduction target fluid.

In this case, the flow analyzer can evaluate the coefficient of diffusion inside the flow container.

(3) In the above flow analyzer, the fluid control section may perform a sine-wave control process on the flow rate or the fluid pressure of the introduction target fluid.

In this case, the flow analyzer can evaluate the residence time of the fluid inside the flow container.

(4) The above flow analyzer may include a plurality of the fluid-introducing sections, and the fluid control section may control the flow rate or the fluid pressure of the introduction target fluids that are introduced into the flow container respectively from two fluid-introducing sections among the plurality of fluid-introducing sections so as to be opposite in phase.

This makes it possible to cyclically change the flow rate or the fluid pressure of the introduction target fluid while ensuring that the flow rate or the fluid pressure of the introduction target fluid is maintained constant.

(5) The above flow analyzer may include a plurality of the fluid-introducing sections, and a plurality of types of the introduction target fluids that have been introduced into the flow container respectively from the plurality of fluid-introducing sections may undergo a reaction inside the flow container.

In this case, the flow analyzer can evaluate the time required for the reaction inside the flow container, or the distribution of the time required for the reaction inside the flow container.

(6) In the above flow analyzer, the flow container may be charged with a catalyst.

(7) According to another embodiment of the invention, there is provided a flow analysis method including:
a fluid control step that performs a control process that cyclically changes a flow rate or a fluid pressure of an introduction target fluid that is introduced into a flow container;
a discharged fluid analysis step that performs a component analysis process on a discharged fluid that has been discharged from the flow container; and
a frequency analysis step that performs a frequency analysis process on a discharge profile, the discharge profile being obtained from control information about the introduction target fluid and analysis results for the discharged fluid, and representing a relationship between a component ratio in the discharged fluid and time.

Since the flow analysis method can evaluate the state inside the flow container by performing the frequency analysis process on the discharge profile, it is possible to easily evaluate the state inside the flow container as compared with the case of evaluating the state inside the flow container using an irreversible analysis process such as an inverse Laplace transform.

(8) In the above flow analysis method, the fluid control step may perform a square-wave control process on the flow rate or the fluid pressure of the introduction target fluid.

In this case, it is possible to evaluate the coefficient of diffusion inside the flow container.

(9) In the above flow analysis method, the fluid control step may perform a sine-wave control process on the flow rate or the fluid pressure of the introduction target fluid.

In this case, it is possible to evaluate the residence time of the fluid inside the flow container.

(10) In the above flow analysis method, the fluid control step may control the flow rate or the fluid pressure of two types of the introduction target fluids to be introduced into the flow container so as to be opposite in phase.

This makes it possible to cyclically change the flow rate or the fluid pressure of the introduction target fluid while ensuring that the flow rate or the fluid pressure of the introduction target fluid is maintained constant.

(11) In the above flow analysis method, a plurality of types of the introduction target fluids may be introduced into the flow container, and the plurality of types of introduction target fluids that have been introduced into the flow container may undergo a reaction inside the flow container.

In this case, it is possible to evaluate the time required for the reaction inside the flow container, or the distribution of the time required for the reaction inside the flow container.

(12) In the above flow analysis method, the flow container may be charged with a catalyst.

Exemplary embodiments of the invention are described in detail below with reference to the drawings. Note that the following exemplary embodiments do not unduly limit the scope of the invention as stated in the claims. Note also that all of the elements described in connection with the following exemplary embodiments should not necessarily be taken as essential elements of the invention.

1. First Embodiment 1.1. Flow Analyzer

A flow analyzer according to a first embodiment is described below with reference to the drawings. FIG. 1 is a view schematically illustrating the configuration of a flow analyzer 100 according to the first embodiment.

As illustrated in FIG. 1, the flow analyzer 100 includes fluid-introducing sections 10a, 10b, and 10c (first fluid-introducing section 10a, second fluid-introducing section 10b, and third fluid-introducing section 10c), a fluid control section 20, a flow container 30, a discharged fluid analysis section 40, and a frequency analysis section 50.

The fluid-introducing sections 10a, 10b, and 10c introduce fluid (introduction target fluid) into the flow container 30. The flow analyzer 100 includes a plurality of fluid-introducing sections (three fluid-introducing sections 10a, 10b, and 10c in the example illustrated in FIG. 1). Note that the number of fluid-introducing sections is not particularly limited.

The first fluid-introducing section 10a includes a first compression container 12a and a first valve 14a. The second fluid-introducing section 10b includes a second compression container 12b and a second valve 14b. The third fluid-introducing section 10c includes a third compression container 12c and a third valve 14c.

The compression containers 12a, 12b, and 12c are cylinders that store fluid. The compression containers 12a, 12b, and 12c store fluid that differs in type. The compression containers 12a, 12b, and 12c are connected to the flow container 30 through a pipe. The pipe is formed of stainless steel, for example.

The valves 14a, 14b, and 14c respectively adjust the flow rate or the fluid pressure of the fluids introduced into the flow container 30 from the compression containers 12a, 12b, and 12c. The first valve 14a is provided to the pipe that connects the first compression container 12a and the flow container 30. The second valve 14b is provided to the pipe that connects the second compression container 12b and the flow container 30. The third valve 14c is provided to the pipe that connects the third compression container 12c and the flow container 30. The valves 14a, 14b, and 14c are solenoid valves, for example. The valves 14a, 14b, and 14c are controlled by the fluid control section 20.

The fluid control section 20 controls the flow rate or the fluid pressure of the fluids introduced into the flow container 30 respectively from the fluid-introducing sections 10a, 10b, and 10c. In the example illustrated in FIG. 1, the fluid control section 20 controls the flow rate or the fluid pressure of the fluids introduced into the flow container 30 respectively from the fluid-introducing sections 10a, 10b, and 10c by controlling the valves 14a, 14b, and 14c.

The fluid control section 20 performs a control process that cyclically changes the flow rate or the fluid pressure of the fluid introduced into the flow container 30 from at least one fluid-introducing section among the fluid-introducing sections 10a, 10b, and 10c. Specifically, the fluid control section 20 performs a control process that modulates the flow rate or the fluid pressure of the fluid introduced into the flow container 30 from at least one fluid-introducing section among the fluid-introducing sections 10a, 10b, and 10c. For example, the fluid control section 20 performs a control process that cyclically changes the flow rate or the fluid pressure of the fluids introduced into the flow container 30 respectively from the first fluid-introducing section 10a and the second fluid-introducing section 10b, and evens out the flow rate or the fluid pressure of the fluid introduced into the flow container 30 from the third fluid-introducing section 10c.

The fluid control section 20 repeats the control process according to a single pattern. For example, the fluid control section 20 performs a square-wave control process on the flow rate or the fluid pressure of the fluid. The term "square-wave control process" used herein refers to a control process that repeatedly sets the valve to an ON state (i.e., a state in which the valve is opened) and an OFF state (i.e., a state in which the valve is closed), and utilizes a square-wave control profile (see FIGS. 3 and 4, for example). Note that the term "control profile" used herein refers to a profile that represents the relationship between the fluid pressure (partial pressure) or the flow rate of the introduction target fluid and time. For example, the fluid control section 20 repeatedly sets the valve to the ON state and the OFF state in a cycle of 0.1 to 3600 seconds.

For example, the fluid control section 20 controls the flow rate or the fluid pressure of the fluids introduced into the flow container 30 respectively from the first fluid-introducing section 10a and the second fluid-introducing section 10b among the fluid-introducing sections 10a, 10b, and 10c so as to be opposite in phase. For example, the fluid control section 20 performs a control process that repeatedly sets the flow rate (or the fluid pressure) of the fluid introduced into the flow container 30 from the first fluid-introducing section 10a to 100% or 0%, sets the flow rate (or the fluid pressure) of the fluid introduced into the flow container 30 from the second fluid-introducing section 10b to 0% when the flow rate (or the fluid pressure) of the fluid introduced into the flow container 30 from the first fluid-introducing section 10a is set to 100%, and sets the flow rate (or the fluid pressure) of the fluid introduced into the flow container 30 from the second fluid-introducing section 10b to 100% when the flow rate (or the fluid pressure) of the fluid introduced into the flow container 30 from the first fluid-introducing section 10a is set to 0%.

The fluid control section 20 may be implemented by a dedicated circuit that performs the above control process. The fluid control section 20 may be implemented by causing a central processing unit (CPU) (i.e., computer) to execute a control program stored in a storage section (not illustrated in the drawings) or the like to perform the above control process.

The flow container 30 is a column (tube-like container) made of glass or stainless steel, for example. The flow container 30 is temperature-controlled, and maintained at a constant temperature, for example. The flow container 30 is charged with a catalyst 32. The catalyst 32 increases the reaction rate of the fluid introduced into the flow container 30. The fluids (that differ in type) introduced into the flow container 30 respectively from the fluid-introducing sections 10a, 10b, and 10c react with each other inside the flow container 30. The fluids introduced into the flow container 30 undergo one or all of an adsorption reaction, a desorption reaction, and an organic reaction inside the flow container 30, and the resulting fluid is discharged from the flow container 30. The flow container 30 serves as a flow reactor in which the fluids that have been introduced undergo a chemical reaction.

The discharged fluid analysis section 40 performs a component analysis process on the fluid (discharged fluid) that has been discharged from the flow container 30. The discharged fluid analysis section 40 acquires component information about the discharged fluid on a time basis as a single index or a spectrum. The discharged fluid analysis section 40 starts the analysis (measurement) in synchronization with the fluid control section 20. Specifically, when the fluid control section 20 has started the control process that controls the flow rate or the fluid pressure of the introduction target fluid, the fluid control section 20 outputs a synchronization signal at a given timing (e.g., at the same timing as the control start timing), and the discharged fluid analysis section 40 receives the synchronization signal, and starts the analysis (measurement). The discharged fluid analysis section 40 is a nuclear magnetic resonance spectrometer, a mass spectrometer, an infrared spectrometer, or an ultraviolet-visible spectrometer, for example. Measurement information (discharge profile) about the discharged fluid that has been measured by the discharged fluid analysis section 40 is transmitted to the frequency analysis section 50 either online or offline.

The frequency analysis section 50 performs a frequency analysis process on the discharge profile calculated from control information about the introduction target fluid and the analysis results for the discharged fluid. Note that the term "discharge profile" used herein refers to a profile that represents the relationship between the ratio of the components included in the discharged fluid and time (elapsed time). The control information about the introduction target fluid is information about the control profile, for example. The control information about the introduction target fluid includes information about a time (base point) $t_0$ at which the valve was switched from the ON state to the OFF state (described later). The analysis results for the discharged fluid are information about the amount (concentration) of each component included in the discharged fluid on a time basis, for example.

Note that the frequency analysis section 50 may acquire the control information about the introduction target fluid and the information about the analysis results for the discharged fluid from the discharged fluid analysis section 40, calculate the discharge profile, and perform the frequency analysis process. The discharged fluid analysis section 40 may calculate the discharge profile from the control information about the introduction target fluid and the analysis results for the discharged fluid, and the frequency analysis section 50 may perform the frequency analysis process on the discharge profile, for example.

It is possible to evaluate the distribution of the efflux time of the fluid inside the flow container 30, and evaluate the state inside the flow container 30 by performing the frequency analysis process on the discharge profile using the frequency analysis section 50, for example. The efflux time (residence time) refers to the time required for the fluid introduced into the flow container 30 to be discharged from the flow container 30. The distribution of the efflux time (residence time) can be evaluated by evaluating the coefficient of diffusion inside the flow container 30.

The frequency analysis section 50 may be implemented by causing a central processing unit (CPU) (i.e., computer) to execute a program stored in a storage section (not illustrated in the drawings) or the like to perform the above process. The frequency analysis section 50 is implemented by a general-purpose computer such as a personal computer (PC), for example.

1.2. Flow Analysis Method

Figure 2:
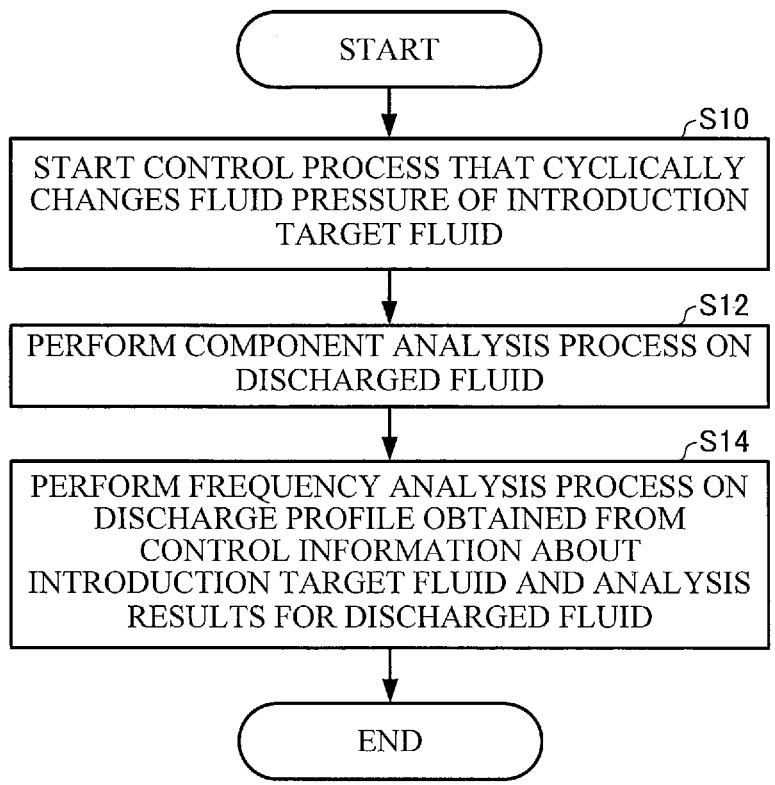
FIG. 2 is a flowchart illustrating an example of a flow analysis method that utilizes a flow analyzer according to the first embodiment.

A flow analysis method that utilizes the flow analyzer according to the first embodiment is described below with reference to the drawings. FIG. 2 is a flowchart illustrating an example of the flow analysis method that utilizes the flow analyzer according to the first embodiment.

Note that the flow analysis method is described below taking an example in which the first fluid-introducing section 10a introduces hydrogen ($H_2$) into the flow container 30, the second fluid-introducing section 10b introduces deuterium ($D_2$) into the flow container 30, the third fluid-introducing section 10c introduces cyclohexene (reactant) into the flow container 30, and a nuclear magnetic resonance spectrometer is used as the discharged fluid analysis section 40. Hydrogen and deuterium are gases, and cyclohexene is a liquid.

The fluid control section 20 starts the control process that cyclically changes the fluid pressure of hydrogen and deuterium introduced into the flow container 30 (step S10).

Figure 3:
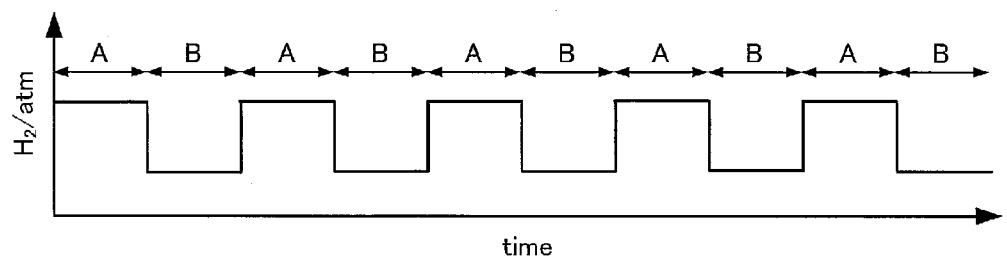
FIG. 3 illustrates a control profile of hydrogen.
Figure 4:
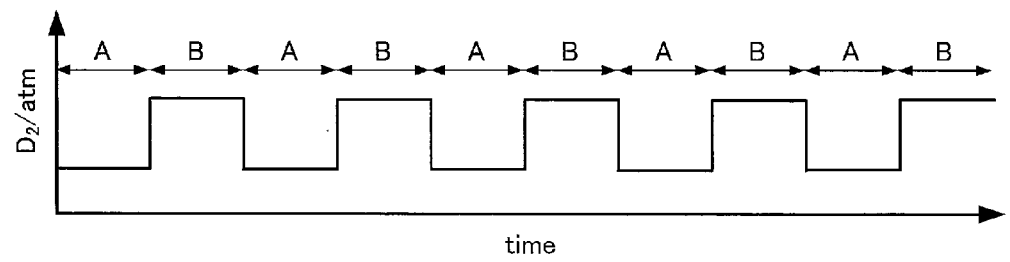
FIG. 4 illustrates a control profile of deuterium.

FIG. 3 is a view illustrating the control profile of hydrogen. FIG. 4 is a view illustrating the control profile of deuterium. In FIGS. 3 and 4, the horizontal axis indicates time, and the vertical axis indicates partial pressure.

The fluid control section 20 controls the valves 14a and 14b so that the fluid pressure of hydrogen is repeatedly set to 100% or 0%, and the fluid pressure of deuterium is set to 0% (state A) when the fluid pressure of hydrogen is set to 100%, and is set to 100% (state B) when the fluid pressure of hydrogen is set to 0% (see FIGS. 3 and 4). The fluid control section 20 controls the third valve 14c so that the fluid pressure of cyclohexene is maintained constant. The fluid control section 20 controls the valves 14a, 14b, and 14c so that hydrogen and cyclohexene or deuterium and cyclohexene are introduced into the flow container 30 at the same time.

The fluid control section 20 controls the valves 14a, 14b, and 14c so that a state in which cyclohexene and hydrogen are introduced into the flow container 30 and a state in which cyclohexene and deuterium are introduced into the flow container 30 occur repeatedly. Note that the flow rate or the fluid pressure of hydrogen introduced into the flow container 30 is maintained constant independently of the state (state A and state B). Specifically, the sum of the flow rate or the fluid pressure of hydrogen and the flow rate or the fluid pressure of deuterium introduced into the flow container 30 at a time t is maintained constant.

Hydrogen and cyclohexene or deuterium and cyclohexene that have been introduced into the flow container 30 come in contact with the catalyst 32, and react with each other inside the flow container 30. For example, a palladium catalyst is used as the catalyst 32.

Figure 5:
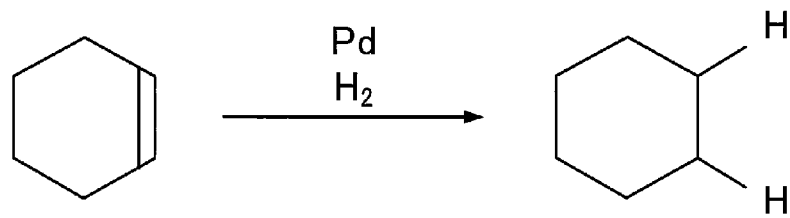
FIG. 5 illustrates an example of a reaction that occurs inside a flow container.
Figure 6:
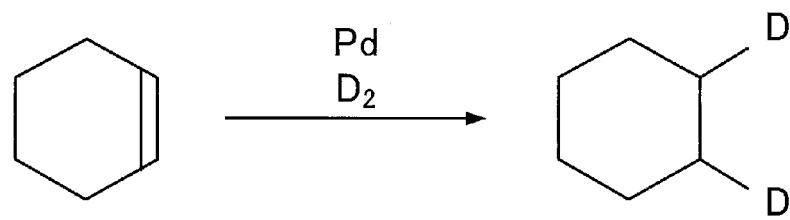
FIG. 6 illustrates an example of a reaction that occurs inside a flow container.

FIGS. 5 and 6 are views illustrating an example of the reaction that occurs inside the flow container 30. As illustrated in FIG. 5, the double bond of cyclohexene is reduced by hydrogen so that cyclohexane is produced. As illustrated in FIG. 6, the double bond of cyclohexene is reduced by deuterium so that cyclohexane-$d_2$ is produced.

When hydrogen or deuterium flows through the flow container 30, adsorption on the catalyst 32, the reaction with cyclohexene, and desorption from the catalyst 32 occur repeatedly, and unreacted hydrogen or deuterium and cyclohexane (reaction product) flow out from the flow container 30 in a mixed state.

Since adsorption on the catalyst 32 and desorption from the catalyst 32 continuously occur, the time required for unreacted hydrogen or deuterium to flow out from the flow container 30 differs from the residence time ($t_r$) inside the flow container 30 due to a diffusion phenomenon. The effects of the diffusion phenomenon are represented by an error function erf that depends on the coefficient of diffusion.

For example, the partial pressure ratio of hydrogen that flows out from the flow container 30 when the state is switched from the state A to the state B at the time $t_0$ is represented by the following expression (1).

$$P_{H_2}(t) = \frac{[\text{erf}\{(t_0 + t_r - t)/D\} + 1]}{2} \times 100\% \quad (1)$$

where, $P_{H2}(t)$ is the response of the ratio of a hydrogen adduct with respect to cyclohexane included in the discharged fluid at the time t when the state is switched from the state A to the state B once, and D is the coefficient of diffusion of hydrogen inside the flow container.

Figure 7:
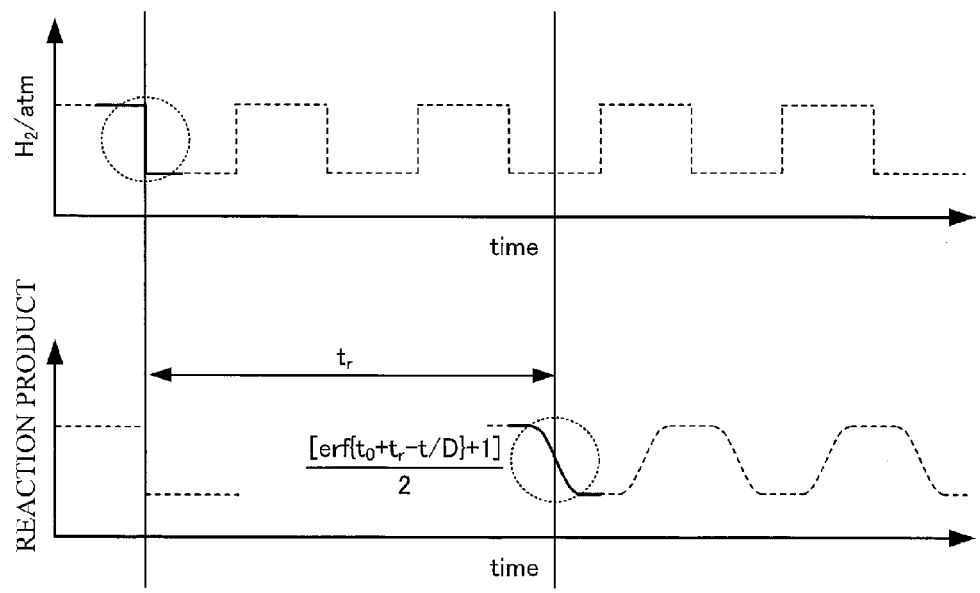
FIG. 7 illustrates the relationship between a control profile of hydrogen and a discharge profile of a reaction product included in a discharged fluid.

FIG. 7 is a view illustrating the relationship between the control profile of the introduction target fluid (hydrogen) and the discharge profile of the reaction product (cyclohexane) included in the discharged fluid. As illustrated in FIG. 7, when the control profile of the introduction target fluid is a square-wave profile, the reaction product (discharged fluid) is discharged according to a functional discharge profile that is represented by the error function. A change (enclosed by the broken line in FIG. 7) in the discharge profile of the reaction product when the state is switched from the state A to the state B is gentle as compared with a change in the control profile when the state is switched from the state A to the state B.

The discharged fluid analysis section 40 performs the component analysis process on the discharged fluid that has been discharged from, the flow container 30 (step S12). The discharged fluid analysis section 40 starts the analysis (measurement) in synchronization with the fluid control process (step S10) performed by the fluid control section 20. For example, the discharged fluid analysis section 40 measures the reaction product included in the discharged fluid by $^1$H-NMR.

Figure 8:
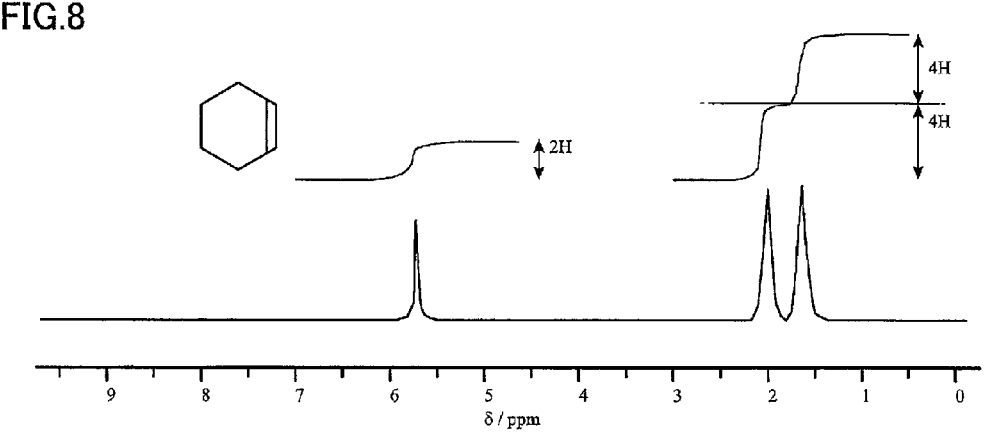
FIG. 8 schematically illustrates the NMR spectrum of cyclohexene.
Figure 9:
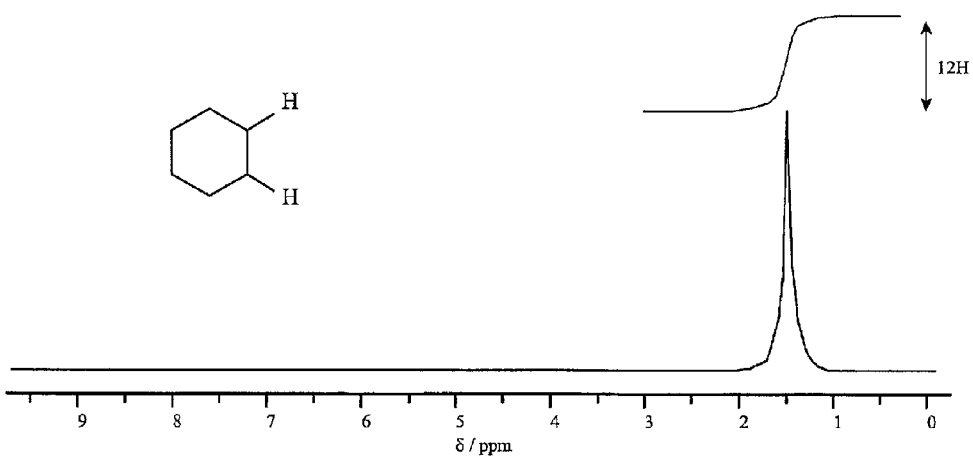
FIG. 9 schematically illustrates the NMR spectrum of cyclohexane.
Figure 10:
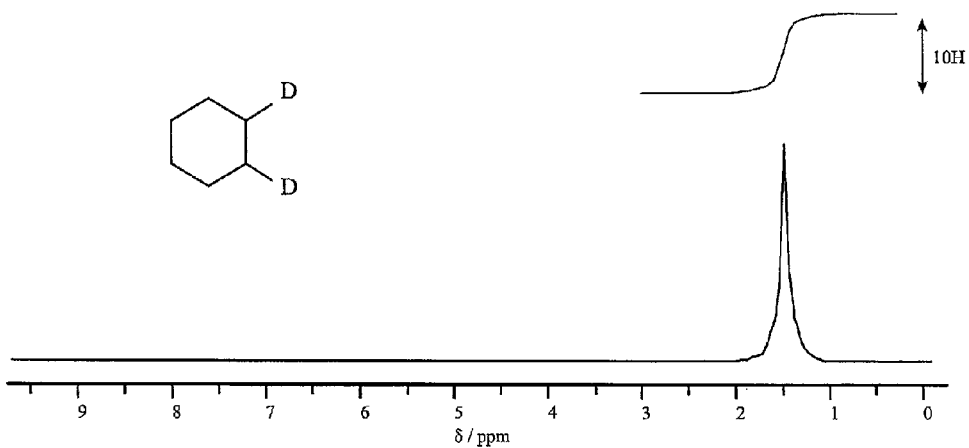
FIG. 10 schematically illustrates the NMR spectrum of cyclohexane-$d_2$.

FIG. 8 is a view schematically illustrating the NMR spectrum of cyclohexene. FIG. 9 is a view schematically illustrating the NMR spectrum of cyclohexane. FIG. 10 is a view schematically illustrating the NMR spectrum of cyclohexane-$d_2$.

The NMR spectrum of the discharged fluid is obtained by adding up the NMR spectrum of cyclohexene illustrated in FIG. 8, the NMR spectrum of cyclohexane illustrated in FIG. 9, and the NMR spectrum of cyclohexane-$d_2$ illustrated in FIG. 10 that are respectively multiplied by Xa, Xb, and Xc. Note that Xa is the ratio of cyclohexene included in the discharged fluid with respect to cyclohexene (=100%) introduced as the introduction target fluid, Xb is the ratio of cyclohexane included in the discharged fluid with respect to cyclohexene (=100%) introduced as the introduction target fluid, Xc is the ratio of cyclohexane-$d_2$ included in the discharged fluid with respect to cyclohexene (=100%) introduced as the introduction target fluid, and Xa+Xb+Xc=100%.

(NMR spectrum of discharged fluid)=Xa×(NMR spectrum of cyclohexene)+Xb×(NMR spectrum of cyclohexane)+Xc×(NMR spectrum of cyclohexane-$d_2$)

In the NMR spectrum of cyclohexene illustrated in FIG. 8, a peak that is not attributed to cyclohexane is observed at around 5.6 ppm. Therefore, the amount of unreacted introduction target fluid (cyclohexene) is obtained from the integral value of the peak at around 5.6 ppm that is observed in the NMR spectrum of the discharged fluid. The amount of cyclohexene introduced as the introduction target fluid is obtained by similarly measuring the NMR spectrum of cyclohexene (introduction target fluid), and the value Xa is obtained by calculating the ratio of the amount of unreacted cyclohexene included in the discharged fluid to the amount of cyclohexene introduced as the introduction target fluid.

For example, when the integral value of the peak at around 5.6 ppm observed in the NMR spectrum of the introduction target fluid is 200, and the integral value of the peak at around 5.6 ppm observed in the NMR spectrum of the discharged fluid is 20, the value Xa is calculated to be 10% (=20/200). Since the size of the peak at around 5.6 ppm corresponds to an integral value that corresponds to a value obtained by multiplying the peak integral value that corresponds to two protons by Xa, the integral value of the peak at around 1.5 to 2 ppm that is attributed to unreacted cyclohexene and observed in the NMR spectrum of the discharged fluid is 80 that corresponds to a value obtained by multiplying the peak integral value that corresponds to eight protons by Xa.

The total ratio of cyclohexane and cyclohexane-$d_2$ in the discharged fluid is 90% that is a value obtained by subtracting the ratio (=10%) of cyclohexene included in the discharged fluid from 100%. Therefore, Xc is (90%−Xb).

In the NMR spectrum of the discharged fluid, the integral value of the peak at around 1.5 to 2 ppm satisfies the following expression.

(Integral value of peak at around 1.5 to 2 ppm/peak integral value that corresponds to one proton)= Xa×8+Xb×12+Xc×10=Xa×8+Xb×12+(100%−Xa−Xb)×10

When the integral value of the peak at around 5.6 ppm observed in the NMR spectrum of the introduction target fluid (cyclohexene: 100%) is 200, the integral value of the peak at around 5.6 ppm observed in the NMR spectrum of the discharged fluid is 20, and the integral value of the peak at around 1.5 to 2 ppm observed in the NMR spectrum of the discharged fluid is 1140, Xa is 10%, Xb is 80%, and Xc is 10%.

1140/(200/2)=0.1×8+Xb×12+(0.9−Xb)×10

Xb=0.8=80%

Xc=0.9−0.8=0.1=10%

The ratio of each component included in the discharged fluid can be calculated from the spectrum of the discharged fluid by performing similar calculations, and the discharge profile can be generated by plotting the ratio of each component with respect to time.

Figure 11A:
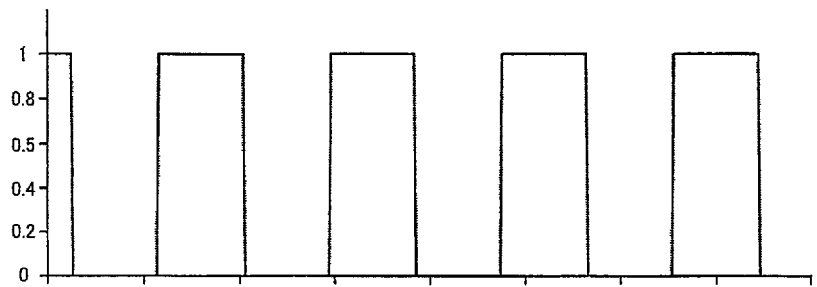
FIG. 11A illustrates a control profile of an introduction target fluid.
Figure 11B:
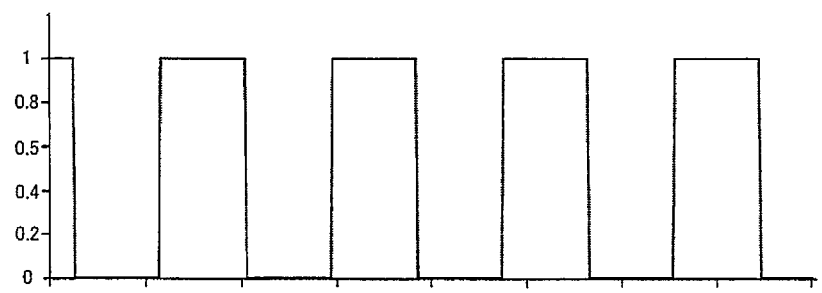
FIGS. 11B, 11C, and 11D illustrate a discharge profile of a reaction component included in a discharged fluid.
Figure 11C:
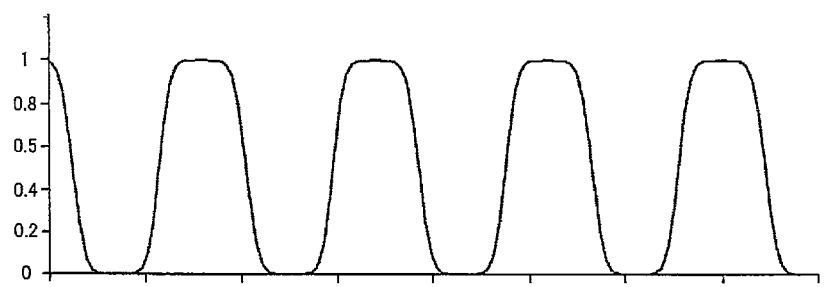
Figure 11D:
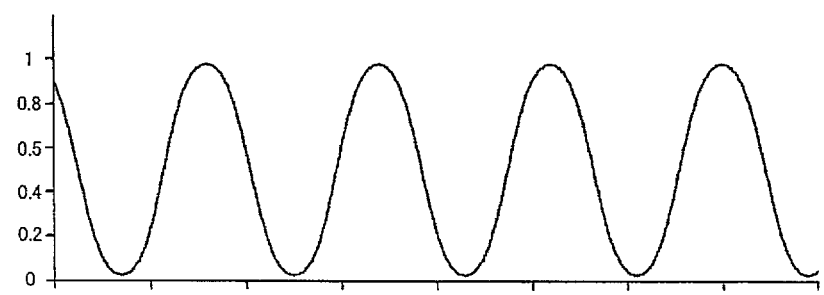

FIG. 11A is a view illustrating the control profile of the introduction target fluid (hydrogen). FIGS. 11B to 11D are views illustrating the discharge profile of the reaction product (cyclohexane) included in the discharged fluid. In FIGS. 11A to 11D, the vertical axis indicates the component ratio, and the horizontal axis indicates the elapsed time. Note that the discharge profiles illustrated in FIGS. 11B to 11D represent the results of simulation. FIG. 11B illustrates the discharge profile when the coefficient of diffusion is smallest, FIG. 11C illustrates the discharge profile when the coefficient of diffusion is medium, and FIG. 11D illustrates the discharge profile when the coefficient of diffusion is largest. The residence time inside the flow container 30 is set to be an integral multiple of the control cycle (1/f) of the introduction target fluid.

As illustrated in FIGS. 11A to 11D, the discharge profile changes more gently when the state is switched as the coefficient of diffusion inside the flow container 30 increases. Note that the discharge profile is shifted to the right as the residence time inside the flow container 30 increases.

The frequency analysis section 50 performs the frequency analysis process on the discharge profile that represents the relationship between the ratio of the component included in the discharged fluid and time (step S14). The frequency analysis section 50 acquires the information about the discharge profile that has been obtained by the discharged fluid analysis section 40, and performs the frequency analysis process on the discharge profile.

The frequency analysis section 50 performs the frequency analysis process by performing a Fourier transform on the discharge profile. If a Fourier transform is applied directly to the discharge profile, sinc function peaks overlap in the resulting frequency characteristics. Therefore, the frequency analysis section 50 performs a Fourier transform after applying a window function so that the peaks can be more easily determined. An exponential decay window function may be used as the window function, for example.

The frequency analysis section 50 performs a process that displays the spectrum obtained by performing a Fourier transform on the discharge profile on a display section (e.g., liquid crystal display (LCD)) (not illustrated in the drawings), for example. The flow analyzer 100 then terminates the process.

Figure 12A:
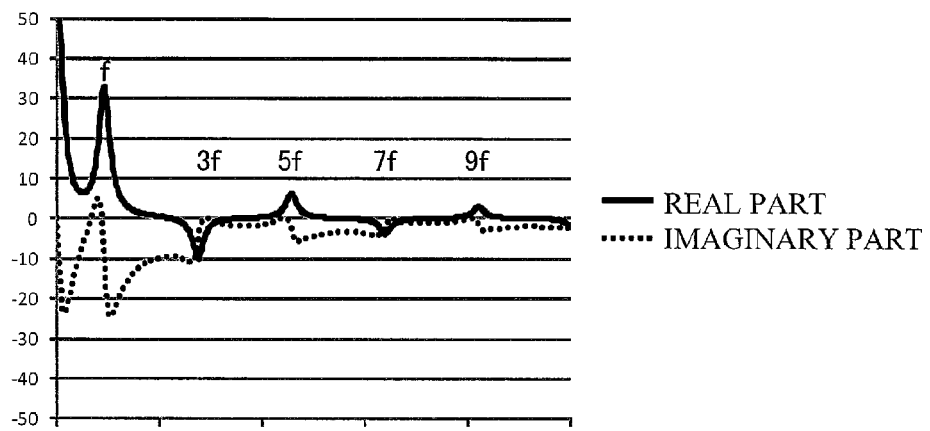
FIG. 12A illustrates the analysis results obtained by applying an exponential decay window function to the discharge profile illustrated in FIG. 11B, and then performing a Fourier transform.
Figure 12B:
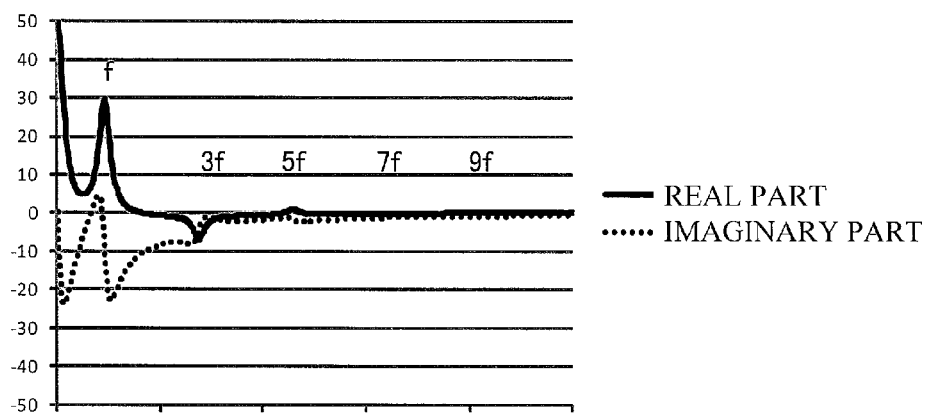
FIG. 12B illustrates the analysis results obtained by applying an exponential decay window function to the discharge profile illustrated in FIG. 11C, and then performing a Fourier transform.
Figure 12C:
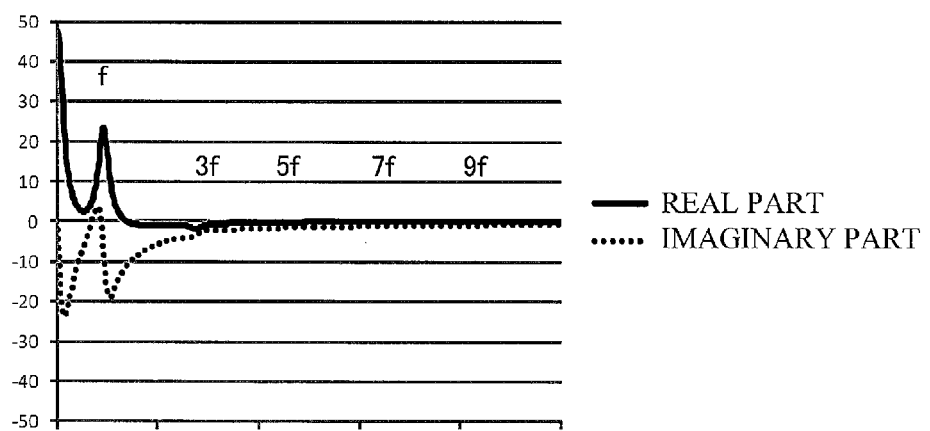
FIG. 12C illustrates the analysis results obtained by applying an exponential decay window function to the discharge profile illustrated in FIG. 11D, and then performing a Fourier transform.

FIG. 12A is a view illustrating the analysis results obtained by applying an exponential decay window function to the discharge profile illustrated in FIG. 11B, and then performing a Fourier transform. FIG. 12B is a view illustrating the analysis results obtained by applying an exponential decay window function to the discharge profile illustrated in FIG. 11C, and then performing a Fourier transform. FIG. 12C is a view illustrating the analysis results obtained by applying an exponential decay window function to the discharge profile illustrated in FIG. 11D, and then performing a Fourier transform.

In the spectra illustrated in FIGS. 12A to 12C, peaks are observed at positions that correspond to odd multiples of the reciprocal of the introduction target fluid switch cycle (1/f). When the ratio of the peak intensity at $3f$, $5f$, $7f$, or $9f$ to the peak intensity at $1f$ is used as an evaluation value, the higher-order peak intensity ratio decreases as the coefficient of diffusion increases, and the coefficient of diffusion inside the flow container 30 can be evaluated.

The coefficient of diffusion depends on the rate of each reaction (adsorption reaction, chemical reaction, and desorption reaction) inside the flow container 30, and a large coefficient of diffusion represents that the distribution of the time required for each reaction is large. Therefore, it is possible to kinetically analyze the reaction inside the flow container 30.

Since the discharged fluid analysis section 40 can determine the amount of each component included in the discharged fluid, it is possible to analyze the distribution of the time required for the reaction corresponding to each component. This makes it possible to analyze a by-product in addition to the main reaction product, and optimize the ratio of the main reaction product that depends on the conditions employed for the flow container 30.

The flow analyzer 100 has the following features, for example.

The flow analyzer 100 is configured so that the fluid control section 20 performs the control process that cyclically changes the flow rate or the fluid pressure of the fluids introduced into the flow container 30 respectively from the fluid-introducing sections 10a, 10b, and 10c, and the frequency analysis section 50 performs the frequency analysis process on the discharge profile calculated from the control information about the introduction target fluid and the analysis results for the discharged fluid. Since the flow analyzer 100 can evaluate the state (e.g., the coefficient of diffusion, and the distribution of the time required for the reaction inside the flow container 30) inside the flow container 30 by performing the frequency analysis process on the discharge profile, it is possible to easily evaluate the state inside the flow container 30 as compared with the case of evaluating the state inside the flow container 30 using an irreversible analysis process such as an inverse Laplace transform. Therefore, the flow analyzer 100 can evaluate the state inside the flow container 30 within a short time, for example.

Since the flow analyzer 100 can evaluate the properties of the fluid inside the flow container 30 by cyclically changing the flow rate or the fluid pressure of the fluid using the fluid control section 20, and performing the frequency analysis process on the discharge profile using the frequency analysis section 50, it is possible to evaluate the state inside the flow container 30 by an in-line process by incorporating the flow analyzer 100 in a flow reactor or the like. Therefore, the flow analyzer 100 can be used to monitor a catalyst in a medicine production line or the like that utilizes a flow reactor, for example. It is also possible to use the flow analyzer 100 for acquiring data used to design a plant that utilizes a flow reactor, for example.

The flow analyzer 100 is configured so that the fluid control section 20 performs the square-wave control process on the flow rate or the fluid pressure of the introduction target fluid. This makes it possible to evaluate the coefficient of diffusion inside the flow container 30. Since the fluid control section 20 repeatedly controls the flow rate or the fluid pressure of the introduction target fluid according to a single pattern (ON-OFF pattern), it is possible to obtain the desired analysis accuracy by increasing the repeat count.

The flow analyzer 100 is configured so that the fluid control section 20 controls the flow rate or the fluid pressure of the fluids introduced into the flow container 30 respectively from the fluid-introducing sections 10a and 10b among the fluid-introducing sections 10a, 10b, and 10c so as to be opposite in phase. This makes it possible to cyclically change the flow rate or the fluid pressure of the introduction target fluid while ensuring that the flow rate or the fluid pressure of the introduction target fluid is maintained constant.

The flow analysis method that utilizes the flow analyzer 100 includes a fluid control step that performs the control process that cyclically changes the flow rate or the fluid pressure of the fluid introduced into the flow container 30 (step S10), a discharged fluid analysis step that performs the component analysis process on the discharged fluid that has been discharged from the flow container 30 (step S12), and a frequency analysis step that performs the frequency analysis process on the discharge profile calculated from the control information about the introduction target fluid and the analysis results for the discharged fluid (step S14). Since the flow analysis method can evaluate the state inside the flow container 30 from the coefficient of diffusion inside the flow container 30 by performing the frequency analysis process on the discharge profile, it is possible to easily evaluate the state inside the flow container 30 as compared with the case of evaluating the state inside the flow container 30 using an irreversible analysis process such as an inverse Laplace transform.

2. Second Embodiment

2.1. Flow Analyzer

A flow analyzer according to a second embodiment is described below. The flow analyzer according to the second embodiment (not illustrated in the drawings) is configured in the same manner as the flow analyzer according to the first embodiment illustrated in FIG. 1. The following description focuses on the differences between the flow analyzer according to the second embodiment and the flow analyzer according to the first embodiment, and description of the same features is omitted.

The flow analyzer 100 according to the first embodiment is configured so that the fluid control section 20 performs the square-wave control process on the flow rate or the fluid pressure of the introduction target fluid.

The flow analyzer according to the second embodiment is configured so that the fluid control section 20 performs a sine-wave (sinusoidal) control process on the flow rate or the fluid pressure of the introduction target fluid. The term "sine-wave control process" used herein refers to a control process that repeatedly sets the valve to an ON state (i.e., a state in which the valve is opened) and an OFF state (i.e., a state in which the valve is closed), and utilizes a sine-wave (sinusoidal) control profile (see FIGS. 13 and 14, for example). For example, the fluid control section 20 repeatedly sets the valve to the ON state and the OFF state in a cycle of 0.1 to 3600 seconds.

For example, the fluid control section 20 controls the flow rate or the fluid pressure of the fluids introduced into the flow container 30 respectively from the first fluid-introducing section 10a and the second fluid-introducing section 10b among the fluid-introducing sections 10a, 10b, and 10c so as to be opposite in phase. For example, the fluid control section 20 performs a control process that repeatedly sets the flow rate (or the fluid pressure) of the fluid introduced into the flow container 30 from the first fluid-introducing section 10a to 100% or 0% in a sinusoidal manner, sets the flow rate (or the fluid pressure) of the fluid introduced into the flow container 30 from the second fluid-introducing section 10b to 0% when the flow rate (or the fluid pressure) of the fluid introduced into the flow container 30 from the first fluid-introducing section 10a is set to 100%, and sets the flow rate (or the fluid pressure) of the fluid introduced into the flow container 30 from the second fluid-introducing section 10b to 100% when the flow rate (or the fluid pressure) of the fluid introduced into the flow container 30 from the first fluid-introducing section 10a is set to 0%.

An electro-pneumatic proportional valve is used as the valves 14a and 14b, for example. This makes it possible to continuously control the flow rate or the fluid pressure of the fluids introduced into the flow container 30 respectively from the fluid-introducing sections 10a and 10b.

2.2. Flow Analysis Method

A flow analysis method that utilizes the flow analyzer according to the second embodiment is described below. The flow analysis method that utilizes the flow analyzer according to the second embodiment differs from the flow analysis method that utilizes the flow analyzer according to the first embodiment (see FIG. 2) in that the fluid control step (step S10) performs the sine-wave control process instead of the square-wave control process described above in connection with the first embodiment. The following description focuses on the difference from the first embodiment, and description of the same features is omitted.

Note that the flow analysis method is described below taking an example in which the first fluid-introducing section 10a introduces hydrogen ($H_2$) into the flow container 30, the second fluid-introducing section 10b introduces deuterium ($D_2$) into the flow container 30, the third fluid-introducing section 10c introduces cyclohexene (reactant) into the flow container 30, and a nuclear magnetic resonance spectrometer is used as the discharged fluid analysis section 40 in the same manner as described above in connection with the first embodiment.

The fluid control section 20 starts the control process that cyclically changes the fluid pressure of hydrogen and deuterium introduced into the flow container 30 (step S10).

Figure 13:
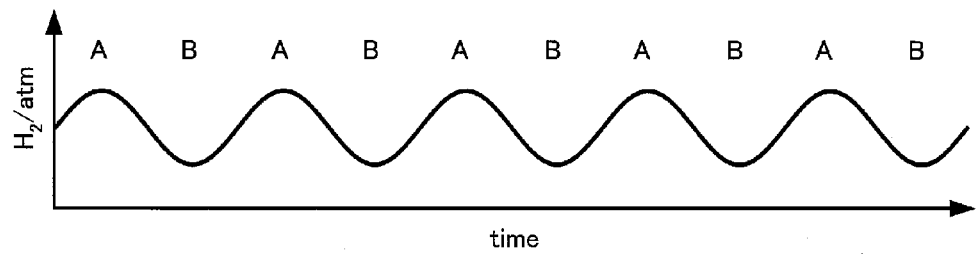
FIG. 13 illustrates a control profile of hydrogen.
Figure 14:
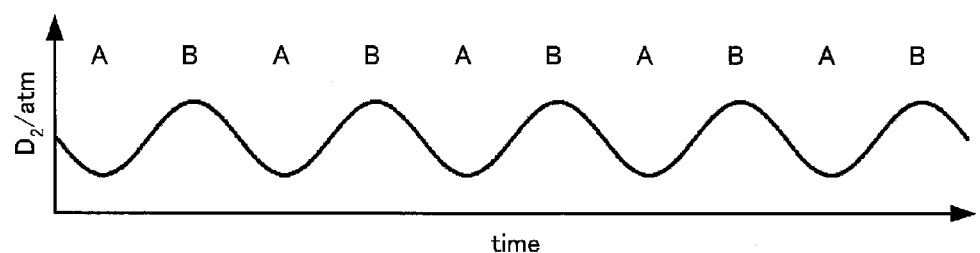
FIG. 14 illustrates a control profile of deuterium.

FIG. 13 is a view illustrating the control profile of hydrogen. FIG. 14 is a view illustrating the control profile of deuterium. In FIGS. 13 and 14, the horizontal axis indicates time, and the vertical axis indicates partial pressure.

The fluid control section 20 performs the control process that repeatedly sets the hydrogen/deuterium partial pressure to "100%/0%" (state A) or "0%/100%" (state B) by alternately opening and closing the first valve 14a and the second valve 14b in a sinusoidal manner. The fluid control section 20 controls the third valve 14c so that the fluid pressure of cyclohexene is maintained constant.

The fluid control section 20 performs the control process so that a state in which cyclohexene and hydrogen are introduced into the flow container 30 and a state in which cyclohexene and deuterium are introduced into the flow container 30 occur repeatedly in a sinusoidal manner. Note that the flow rate or the fluid pressure of hydrogen introduced into the flow container 30 is maintained constant independently of the state (state A and state B). Specifically, the sum of the flow rate or the fluid pressure of hydrogen and the flow rate or the fluid pressure of deuterium introduced into the flow container 30 at a time t is maintained constant.

Hydrogen and cyclohexene or deuterium and cyclohexene that have been introduced into the flow container 30 come in contact with the catalyst 32 (palladium catalyst), and react with each other inside the flow container 30. The double bond of cyclohexene is reduced by hydrogen so that cyclohexane is produced (see FIG. 5). The double bond of cyclohexene is reduced by deuterium so that cyclohexane-$d_2$ is produced (see FIG. 6).

When hydrogen or deuterium flows through the flow container 30, adsorption on the catalyst 32, the reaction with cyclohexene, and desorption from the catalyst 32 occur repeatedly, and unreacted hydrogen or deuterium and cyclohexane (reaction product) flow out from the flow container 30 in a mixed state.

Since adsorption on the catalyst 32 and desorption from the catalyst 32 continuously occur, the residence time ($t_r$) (i.e., the time required for unreacted hydrogen or deuterium to flow out from the flow container 30) depends on the flow rate of the fluid inside the flow container 30, and the rate of the adsorption reaction, the synthesis reaction, and the desorption reaction. Specifically, the residence time increases as the reaction takes more time.

The difference in residence time is detected as the difference between the control profile of the introduction target fluid and the discharge profile of the reaction product included in the discharged fluid. For example, the partial pressure ratio of hydrogen that flows out when the state is switched from the state A to the state B at the time $t_0$ in a sinusoidal manner is represented by the expression (1).

The relationship between the control profile (control profile of hydrogen) $P_{in}(t)$ of the partial pressure ratio of hydrogen with respect to hydrogen introduced as the introduction target fluid at the time t and the discharge profile (discharge profile of hydrogen) $P_{out}(t)$ of the partial pressure ratio of hydrogen with respect to hydrogen included in the discharged fluid at the time t is represented by the following expression (2).

$$P_{out}(t-t_0) = P_{in}(t-t_0-t_r) \qquad (2)$$

Figure 15A:
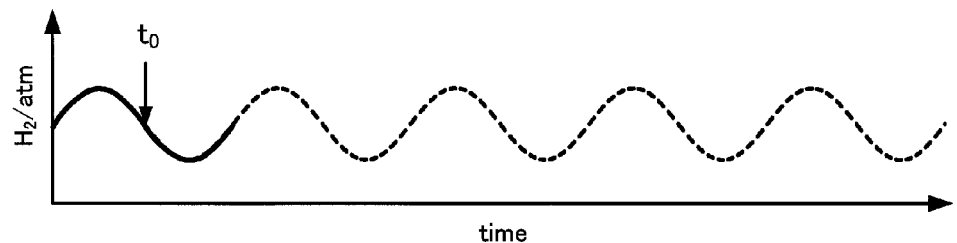
FIG. 15A illustrates a control profile of an introduction target fluid.
Figure 15B:
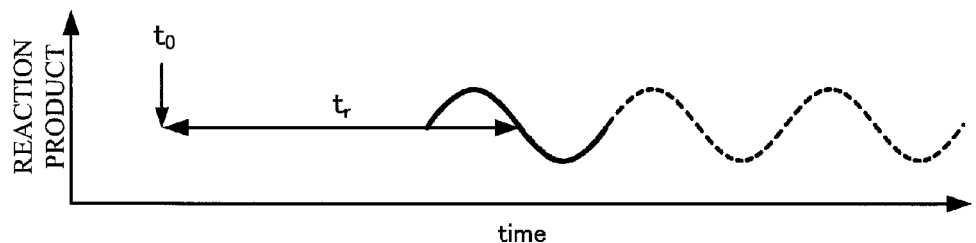
FIGS. 15B, 15C, and 15D illustrate a discharge profile of a reaction component included in a discharged fluid.
Figure 15C:
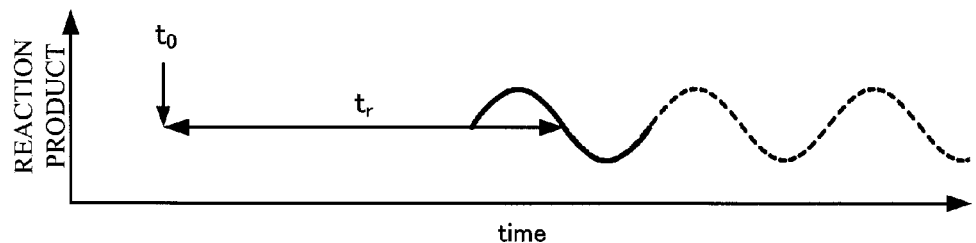
Figure 15D:
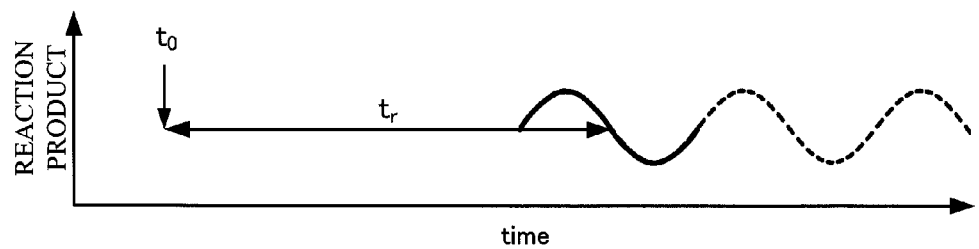

FIGS. 15A to 15D are views illustrating the relationship between the control profile $P_{in}$ of the introduction target fluid (hydrogen) and the discharge profile $P_{out}$ of the reaction product (cyclohexane) included in the discharged fluid. FIG. 15A is a view illustrating the control profile of the introduction target fluid. FIGS. 15B to 15D are views illustrating the discharge profile of the reaction product (cyclohexane) included in the discharged fluid. In FIGS. 15A to 15D, the vertical axis indicates the partial pressure ratio, and the horizontal axis indicates the elapsed time. FIG. 15B illustrates the discharge profile when the residence time is shortest, FIG. 15C illustrates the discharge profile when the residence time is medium, and FIG. 15D illustrates the discharge profile when the residence time is longest.

When the introduction target fluid is controlled in a sinusoidal manner (see FIG. 15A), the discharged fluid is discharged according to a functional discharge profile that is represented by the same sine wave (see FIGS. 15B to 15D). Note that the base point of the discharge profile is shifted corresponding to the residence time that depends on the flow rate and the reaction time inside the flow container 30. As illustrated in FIGS. 15B to 15D, the base point of the discharge profile is shifted to the right as the residence time increases.

When the discharge time varies due to a diffusion phenomenon (see the first embodiment), the distribution of the partial pressure ratio (vertical axis) of the discharge profile increases with respect to time. Therefore, a change in the partial pressure ratio of the discharge profile is time-averaged and decreases as the coefficient of diffusion increases.

The discharged fluid analysis section 40 performs the component analysis process on the discharged fluid that has been discharged from the flow container 30 (step S12). In the step S12, the discharged fluid analysis section 40 performs the component analysis process on the discharged fluid in the same manner as described above in connection with the first embodiment. The discharge profiles illustrated in FIGS. 15B to 15D are thus obtained.

The frequency analysis section 50 performs the frequency analysis process on the discharge profile that represents the relationship between the ratio of the component included in the discharged fluid and time (step S14). In the step S14, the frequency analysis section 50 performs the frequency analysis process on the discharge profile of the reaction product included in the discharged fluid in the same manner as described above in connection with the first embodiment.

Figure 16A:
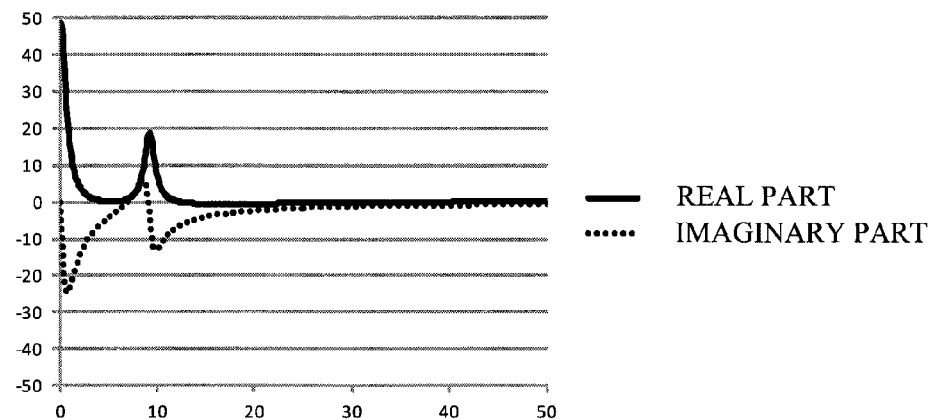
FIG. 16A illustrates the analysis results obtained by applying an exponential decay window function to the discharge profile illustrated in FIG. 15B, and then performing a Fourier transform.
Figure 16B:
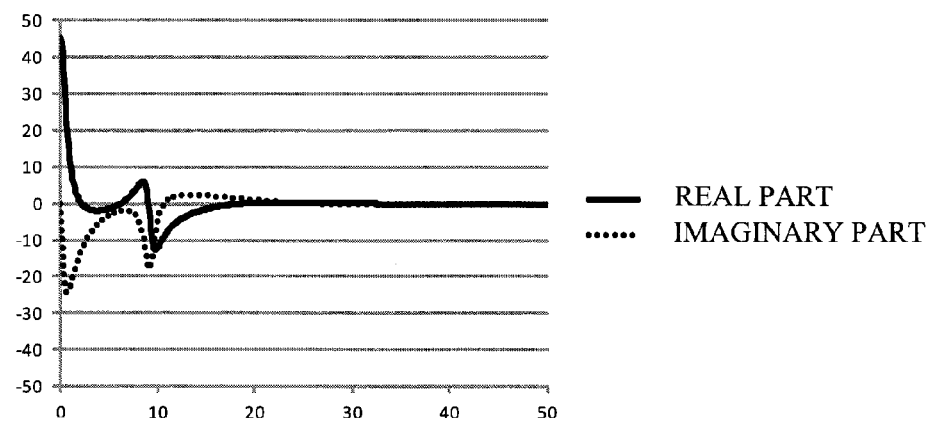
FIG. 16B illustrates the analysis results obtained by applying an exponential decay window function to the discharge profile illustrated in FIG. 15C, and then performing a Fourier transform.
Figure 16C:
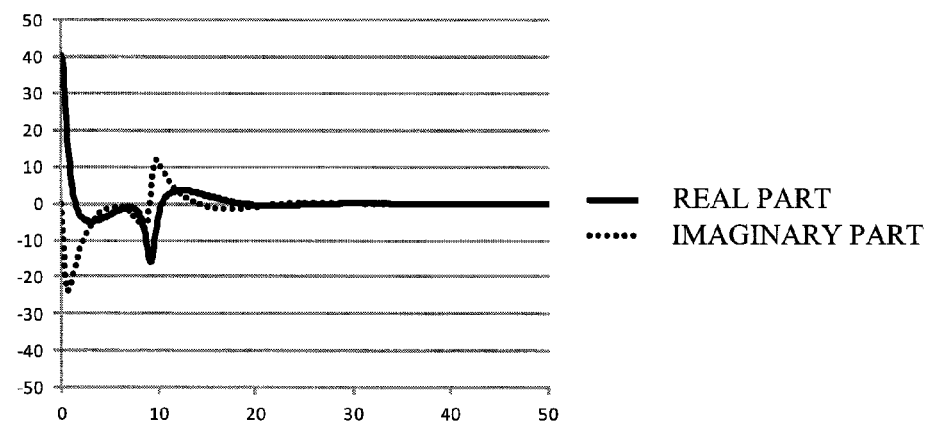
FIG. 16C illustrates the analysis results obtained by applying an exponential decay window function to the discharge profile illustrated in FIG. 15D, and then performing a Fourier transform.

FIG. 16A is a view illustrating the analysis results obtained by applying an exponential decay window function to the discharge profile illustrated in FIG. 15B, and then performing a Fourier transform. FIG. 16B is a view illustrating the analysis results obtained by applying an exponential decay window function to the discharge profile illustrated in FIG. 15C, and then performing a Fourier transform. FIG. 16C is a view illustrating the analysis results obtained by applying an exponential decay window function to the discharge profile illustrated in FIG. 15D, and then performing a Fourier transform.

As illustrated in FIGS. 16A to 16C, the phase of the peak that appears at the same frequency as that of the control profile changes depending on the residence time inside the flow container 30. The phase of the peak is the same as that of the control profile when the residence time is an integral multiple of the cycle of the control profile, but is shifted in the positive direction as the residence time increases. The difference in residence time can be analyzed from the change in phase within the same range as that of the cycle of the control profile. Note that the difference in residence time can be analyzed over a wider range by increasing the cycle of the control profile, or analyzing the difference in residence time from a plurality of results obtained while changing the cycle of the control profile.

The analysis results for the residence time depend on the rate of each reaction (adsorption reaction, chemical reaction, and desorption reaction) inside the flow container 30, and a long residence time means that much time is required for each reaction. Therefore, it is possible to kinetically analyze the reaction inside the flow container 30.

It is possible to analyze the time required for the reaction corresponding to each component by determining the amount of each component included in the discharged fluid using the discharged fluid analysis section 40. This makes it possible to analyze a by-product in addition to the main reaction product, and optimize the ratio of the main reaction product that depends on the conditions employed for the flow container 30.

Since the flow analyzer according to the second embodiment can evaluate the state (e.g., the residence time, and the time required for the reaction inside the flow container 30) inside the flow container 30 by performing the frequency analysis process on the discharge profile, it is possible to easily evaluate the state inside the flow container 30 as compared with the case of evaluating the state inside the flow container 30 using an irreversible analysis process such as an inverse Laplace transform. Therefore, the flow analyzer according to the second embodiment can evaluate the state inside the flow container 30 within a short time, for example.

The flow analyzer according to the second embodiment is configured so that the fluid control section 20 performs the sine-wave control process on the flow rate or the fluid pressure of the introduction target fluid. This makes it possible to evaluate the residence time as described above. Since the flow analyzer according to the second embodiment can evaluate the state inside the flow container 30 by evaluating the residence time of the fluid inside the flow container 30, it is possible to easily evaluate the state inside the flow container 30 as compared with the case of evaluating the state inside the flow container 30 using an irreversible analysis process such as an inverse Laplace transform.

The invention is not limited to the above embodiments. Various modifications and variations may be made of the above embodiments without departing from the scope of the invention.

Although the first embodiment has been described above taking an example in which the fluid control section 20 performs the square-wave control process on the flow rate dr the fluid pressure of the introduction target fluid, and the second embodiment has been described above taking an example in which the fluid control section 20 performs the sine-wave control process on the flow rate or the fluid pressure of the introduction target fluid, the control process performed by the fluid control section 20 is not particularly limited as long as the fluid control section 20 can cyclically change the flow rate or the fluid pressure of the introduction target fluid. Specifically, the control profile is not limited to the square-wave control profile and the sine-wave control profile, and may be appropriately set taking account of the object of analysis.

Although the first embodiment and the second embodiment have been described above taking an example in which hydrogen, deuterium, and cyclohexene are introduced into the flow container 30, the type of fluid that is introduced into the flow container 30 is not particularly limited. For example, only liquid may be introduced into the flow container 30, or only gas may be introduced into the flow container 30. Although FIG. 1 illustrates an example in which the fluid is introduced into the upper part of the flow container 30, and discharged from the lower part of the flow container 30, the fluid may be introduced into the lower part of the flow container 30, and discharged from the upper part of the flow container 30 when introducing liquid into the flow container 30.

Although the first embodiment and the second embodiment have been described above taking an example in which the flow container 30 is charged with the catalyst 32 so that the fluids can be reacted, the fluids may not be reacted inside the flow container 30. For example, fluid may be introduced into the flow container 30 that is charged with a porous polymer while cyclically changing the flow rate or the fluid pressure of the fluid using the fluid control section 20, the discharged fluid may be analyzed using the discharged fluid analysis section 40, and the frequency analysis process may be performed on the discharge profile using the frequency analysis section 50 to evaluate adsorption of the fluid on the porous polymer, desorption of the fluid from the porous polymer, and the like.

The invention includes various other configurations substantially the same as the configurations described in connection with the above embodiments (e.g., a configuration having the same function, method, and results, or a configuration having the same objective and effects). The invention also includes a configuration in which an unsubstantial element (part) described in connection with the above embodiments is replaced by another element (part). The invention also includes a configuration having the same effects as those of the configurations described in connection with the above embodiments, or a configuration capable of achieving the same objective as that of the configurations described in connection with the above embodiments. The invention further includes a configuration in which a known technique is added to the configurations described in connection with the above embodiments.

Although only some embodiments of the invention have been described in detail above, those skilled in the art would readily appreciate that many modifications are possible in the embodiments without materially departing from the novel teachings and advantages of the invention. Accordingly, all such modifications are intended to be included within the scope of the invention.

What is claimed is:

1. A flow analyzer comprising:
  a processor;
  a flow container;
  a fluid-introducing section that introduces an introduction target fluid into the flow container;
  a fluid control section comprising a stored program comprising instructions to instruct the processor to perform a control process that cyclically changes a flow rate or a fluid pressure of one or more introduction target fluids introduced into the flow container from the fluid-introducing section;
  a discharged fluid analysis section that performs a component analysis process on a discharged fluid that has been discharged from the flow container; and
  a frequency analysis section comprising a stored program comprising instructions to instruct the processor to perform a frequency analysis process on a discharge profile of the discharged fluid by, (1) obtaining control information about the introduction target fluid and the analysis results of the discharged fluid analysis section, (2) determining the discharge profile from control information about the introduction target fluid and analysis results for the discharged fluid, and representing a relationship between a component ratio in the discharged fluid and time, and (3) performing a frequency analysis on said discharge profile.

2. The flow analyzer as defined in claim 1,
wherein the stored program of the fluid control section comprises instructions to instruct the processor to perform a square-wave control process on the flow rate or the fluid pressure of the introduction target fluid.

3. The flow analyzer as defined in claim 1,
wherein the stored program of the fluid control section comprises instructions to instruct the processor to perform a sine-wave control process on the flow rate or the fluid pressure of the introduction target fluid.

4. The flow analyzer as defined in claim 1,
The flow analyzer comprising a plurality of the fluid-introducing sections for introducing a plurality of introduction target fluids,
wherein the stored program of the fluid control section comprises instructions to instruct the processor to control the flow rate or the fluid pressure of the introduction target fluids that are introduced into the flow container respectively from two fluid-introducing sections among the plurality of fluid-introducing sections so as to be opposite in phase.

5. The flow analyzer as defined in claim 1,
the flow analyzer comprising a plurality of the fluid-introducing sections for introducing a plurality of introduction target fluids,
wherein a plurality of types of the introduction target fluids that have been introduced into the flow container respectively from the plurality of fluid-introducing sections undergo a reaction inside the flow container.

6. The flow analyzer as defined in claim 1,
wherein the flow container is charged with a catalyst.

7. A flow analysis method comprising:
  a fluid control step that performs a control process that cyclically changes a flow rate or a fluid pressure of one or more introduction target fluids introduced into a flow container;
  a discharged fluid analysis step that performs a component analysis process on discharged fluid that has been discharged from the flow container; and
  a frequency analysis step that performs a frequency analysis process on a discharge profile, the discharge profile being obtained from control information about the introduction target fluid and analysis results for the discharged fluid, and representing a relationship between a component ratio in the discharged fluid and time.

8. The flow analysis method as defined in claim 7,
wherein the fluid control step performs a square-wave control process on the flow rate or the fluid pressure of the introduction target fluid.

9. The flow analysis method as defined in claim 7,
wherein the fluid control step performs a sine-wave control process on the flow rate or the fluid pressure of the introduction target fluid.

10. The flow analysis method as defined in claim 7,
wherein the fluid control step controls the flow rate or the fluid pressure of two types of the introduction target fluids to be introduced into the flow container so as to be opposite in phase.

11. The flow analysis method as defined in claim 7, wherein a plurality of types of the introduction target fluids are introduced into the flow container, and the plurality of types of introduction target fluids that have been introduced into the flow container undergo a reaction inside the flow container.

12. The flow analysis method as defined in claim 7, wherein the flow container is charged with a catalyst.

\* \* \* \* \*